(12) United States Patent
Tanaka

(10) Patent No.: US 8,214,758 B2
(45) Date of Patent: Jul. 3, 2012

(54) INFORMATION PROCESSING APPARATUS, METHOD OF CONTROL FOR SAME, AND PROGRAM

(75) Inventor: Hirokazu Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 242 days.

(21) Appl. No.: 12/708,364

(22) Filed: Feb. 18, 2010

(65) Prior Publication Data

US 2010/0223573 A1    Sep. 2, 2010

(30) Foreign Application Priority Data

Mar. 2, 2009 (JP) .................. 2009-048510

(51) Int. Cl.
*G06F 3/048* (2006.01)
*G06F 7/38* (2006.01)

(52) U.S. Cl. .................. 715/777; 715/802; 708/524
(58) Field of Classification Search .................. 715/777, 715/802; 708/524
See application file for complete search history.

(56) References Cited

U.S. PATENT DOCUMENTS

| | | | |
|---|---|---|---|
| 6,775,577 B2 * | 8/2004 | Crnkovich et al. | 700/11 |
| 2002/0114429 A1 * | 8/2002 | Engelke et al. | 379/88.01 |
| 2003/0014467 A1 * | 1/2003 | Hanzawa | 709/102 |
| 2005/0097506 A1 * | 5/2005 | Heumesser | 717/102 |
| 2005/0149936 A1 * | 7/2005 | Pilkington | 718/102 |
| 2006/0080619 A1 * | 4/2006 | Carlson et al. | 715/781 |
| 2006/0133362 A1 * | 6/2006 | Stein et al. | 370/360 |
| 2006/0271858 A1 * | 11/2006 | Yolleck et al. | 715/738 |
| 2008/0180743 A1 * | 7/2008 | Uruta et al. | 358/1.15 |
| 2010/0177345 A1 * | 7/2010 | Watanabe | 358/1.15 |

FOREIGN PATENT DOCUMENTS

| | | | |
|---|---|---|---|
| JP | 2003-245270 | * | 9/2003 |
| JP | 2003-245270 A | | 9/2003 |

* cited by examiner

*Primary Examiner* — William Bashore
*Assistant Examiner* — Andrea Long
(74) *Attorney, Agent, or Firm* — Canon USA Inc IP Division

(57) ABSTRACT

An information processing apparatus is configured to execute a plurality of operations in parallel. A display unit displays a header identifying each operation in a plurality of operation on a display unit. A control unit switches a current operation based on selection of the header via an input unit and, when switching the current operation, controls display of suspension information to indicate a suspension state of a suspended operation on the header for the suspended operation in addition to the current operation.

18 Claims, 17 Drawing Sheets

FIG. 12

| TAB | SUSPEND INFORMATION | CURRENT TAB |
|---|---|---|
| 1 | 0:00:00 | 1 |
| 2 | 0:03:26 | 0 |
| ∗ | ∗ | ∗ |
| ∗ | ∗ | ∗ |
| ∗ | ∗ | ∗ |

FIG. 15

| TAB | SUSPEND INFORMATION | CURRENT TAB | SUSPEND INFORMATION DISPLAY |
|---|---|---|---|
| 1 | 0:00:00 | 1 | 1 |
| 2 | 0:02:25 | 0 | 1 |
| 3 | 0:00:00 | 0 | 0 |
| 4 | 0:08:14 | 0 | 1 |
| . | . | . | . |

INFORMATION PROCESSING APPARATUS, METHOD OF CONTROL FOR SAME, AND PROGRAM

BACKGROUND OF THE INVENTION

1. Field of the Invention

The present invention relates to an information processing apparatus configured to execute parallel processing of a plurality of operations, a method of control for the same and a program configured to cause a computer to execute the control method.

2. Description of the Related Art

Currently there is a range of conventional information processing systems from wide spread personal computers (hereafter "PC") to exclusive use systems for specific areas. Such information processing systems are designed for simultaneous execution of a plurality of operations.

Normally such information processing systems are configured to use a graphical user interface (hereafter "GUI") to enable selection of the operation from a plurality of operations executed in parallel, which is to be designated as the current operation. Thereafter, an operator can execute operations on the current operation. With this arrangement, other operations which are not designated as current are in a suspension state and cannot be the object of operations until the GUI is used to place the undesignated operation in a current state.

For example, widely-used PCs are configured to enable parallel execution of a plurality of operations including word processing and spreadsheets. A user can switch between a plurality of operations using a GUI called a taskbar which is provided on the screen. More specifically, an operation title or icon is displayed on the taskbar as a display component (header) configured to identify the operation. By selecting a title or icon, the user can switch the current operation.

Additionally, exclusive use systems for specific areas such as X-ray imaging systems are configured to enable parallel operation of examining X-ray images or display of previously-imaged historical images. Prior to commencement of examination of a given patient and completion of all related X-ray imaging, examining of another patient with a higher priority level may have to be interposed and consequently there is a need for parallel execution of examining a plurality of patients. After examining is commenced, the GUI adds an examining tab as a display component (header) identifying the operation on the GUI. When the examining is completed, the tab for that examination is deleted. Information configured to specify the examination such as the patient name or examination ID is displayed on the tab. Prior to completion of the examination, when examining of a subsequent patient is commenced, the examination tab for the patient who is being examined is placed in a non-selected state and a tab for the new examination is added. A plurality of examinations may be suspended at this time and the suspended examinations may be recommenced by using the GUI to select the examination tab of the examination to be recommenced.

Another example of an X-ray imaging system is discussed in Japanese Patent Application Laid-Open No. 2003-245270 in which after a first examination which is being executed is suspended and another examination is executed, the suspended examination is recommenced. The example disclosed in Japanese Patent Application Laid-Open No. 2003-245270 is configured to enable recommencement of suspended examinations by using the GUI to select a suspended examination from a "reservation reception list screen".

Conventional information processing systems executing a plurality of operations in the above manner enable display and selection on a GUI of components (headers) such as a tab, list or task bar configured to identify operations and to thereby select a current operation. Since a selected state or a non-selected state of these display components can be distinguished and displayed as suspended on the list, an operator can understand which operations are suspended.

However a conventional information processing system does not notify the suspension period of particular operations and no information is available to decide which operation to recommence next. As a result, the problem arises that an operation may remain uncompleted for a long time. In particular, when the system is applied to an X-ray imaging system, a patient may wait for an unnecessarily long period of time. In addition, there is the problem that the suspended operations cannot be divided into operations which need not be completed and operations which must be completed.

SUMMARY OF THE INVENTION

The present invention is directed to a system configured to prevent a suspended operation from remaining unexecuted when executing processing of a plurality of operations at the same time.

An information processing apparatus configured to execute a plurality of operations in parallel includes a display unit configured to display a header which identifies each operation in a plurality of operations, a switching unit configured to switch a current operation based on selection of the header, and a display control unit which, when a current operation is switched using the switching unit, controls display of suspension information to indicate a suspension state of a suspended operation on the header for a suspended operation in addition to the current operation.

Further features and aspects of the present invention will become apparent from the following detailed description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 12 is a schematic diagram illustrating an example of a suspension information table managed by an X-ray imaging system (information processing system) according to the first embodiment of the present invention.

FIG. 15 is a schematic diagram illustrating an example of a suspension information table managed by an X-ray imaging system (information processing system) according to the second embodiment of the present invention.

DESCRIPTION OF THE EMBODIMENTS

Various exemplary embodiments, features, and aspects of the invention will be described in detail below with reference to the drawings.

An X-ray imaging system will be used as an example to describe the information processing system according to the present invention with respect to each embodiment of the present invention described hereafter.

Figure 1:
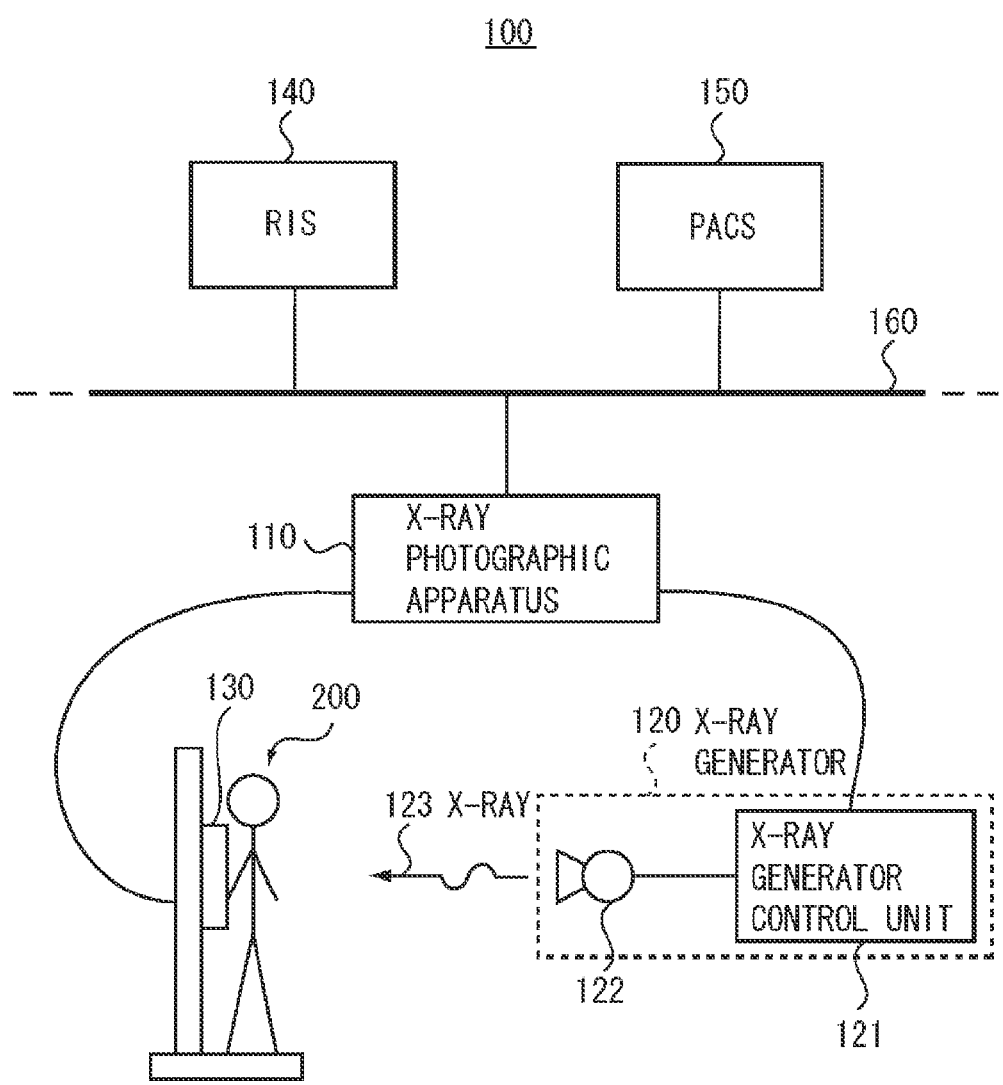
FIG. 1 is a schematic diagram illustrating an example overview of an X-ray imaging system (information processing system) according to a first embodiment of the present invention.

Firstly a first embodiment of the present invention will be described. FIG. 1 is a schematic diagram illustrating an example of the general overview of an X-ray imaging system (information processing system) according to a first embodiment of the present invention.

As illustrated in FIG. 1, an X-ray imaging system 100 includes an X-ray imaging apparatus 110, an X-ray generator 120, an X-ray detection apparatus 130, a radiology information system (RIS) 140, a picture archiving and information system (PACS) 150 and a hospital local network 160.

The X-ray imaging apparatus 110 is an information processing apparatus which is connected to the hospital local network 160 and which is configured to communicate information with the RIS 140 and PACS 150. The X-ray imaging apparatus 110 is connected to enable communication with the X-ray generator 120 and the X-ray detection apparatus 130.

For example, the X-ray imaging apparatus 110 receives examination order from the RIS 140 to be executed by the X-ray imaging apparatus 110. The X-ray generator 120 and the X-ray detection apparatus 130 are controlled in accordance with the examination order to thereby execute an examination by X-ray imaging of a patient 200 who is the object of the examining operation. More specifically, the X-ray imaging apparatus 110 sends X-ray generation conditions including an emission period of X-rays 123 emitted from the X-ray tube 122, an X-ray tube voltage and an X-ray tube current of the X-ray tube 122, to an X-ray generator control unit 121 of the X-ray generator 120.

The X-ray generator 120 generates X-rays 123 and is formed from the X-ray generator control unit 121 and the X-ray tube 122. The X-ray generator control unit 121 controls the X-ray tube 122 in accordance with the X-ray generation conditions sent from the X-ray imaging apparatus 110. The X-ray tube 122, under the control of the X-ray generator control unit 121, generates X-rays 123 with reference to a patient 200 who is the object to be imaged.

The X-ray detection apparatus (X-ray sensor) 130 detects X-rays transmitted through the patient 200 as a digital image. Then the X-ray imaging apparatus 110 receives the digital image output from the X-ray detection apparatus 130, executes required processing on the digital image and then sends the resulting image as a medical image to a PACS 150 for example.

The RIS 140 is a radiological information system configured to manage examination orders from various diagnosis and treatment departments.

The PACS 150 is configured to collect and manage medical images from a range of modalities (such as the X-ray imaging apparatus 110) connected to the hospital local network 160.

Figure 2:
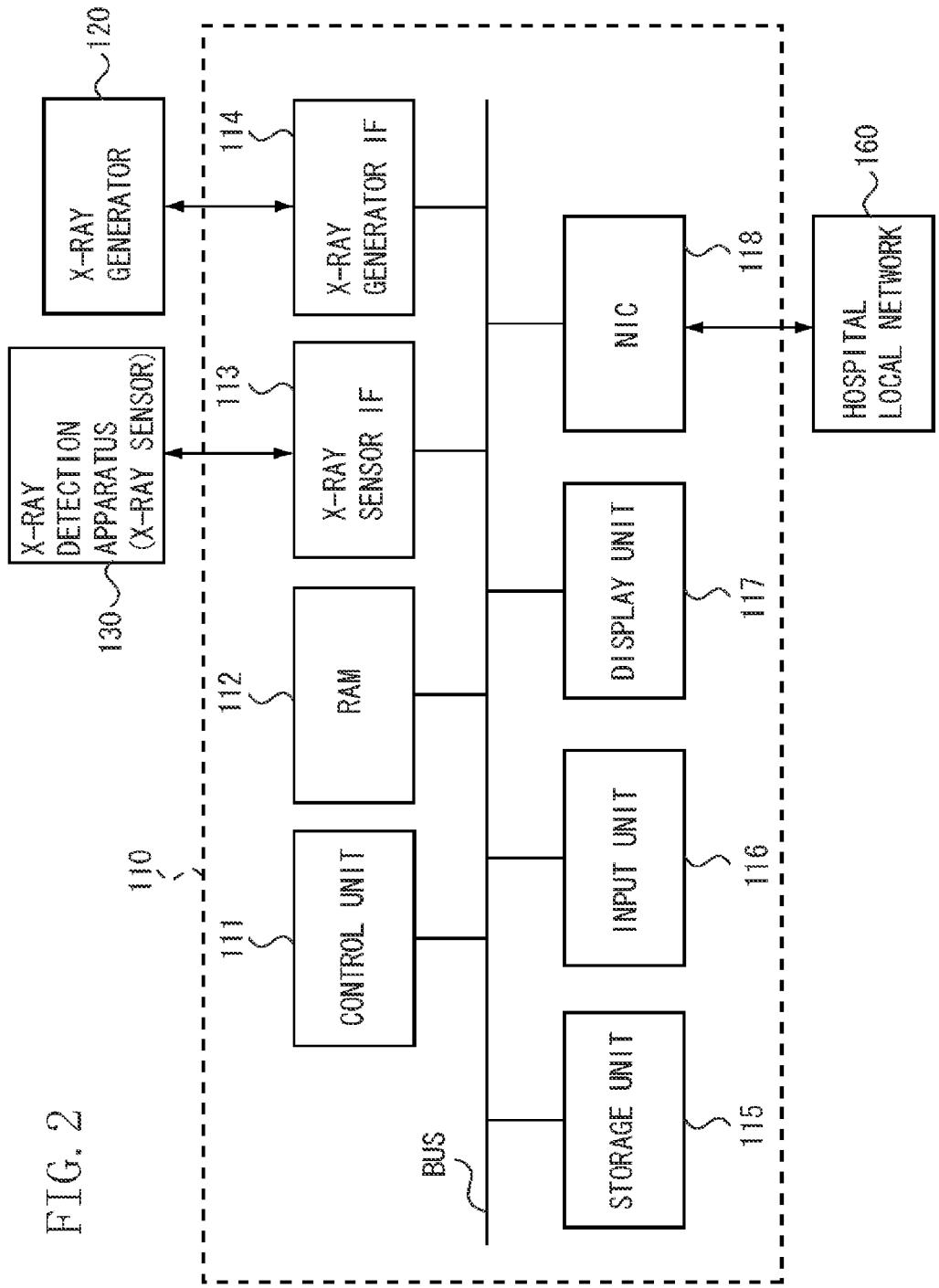
FIG. 2 is a schematic diagram illustrating an example of the inner arrangement of an X-ray imaging system (information processing system) according to the first embodiment of the present invention.

FIG. 2 is a schematic diagram illustrating an example of the inner arrangement of an X-ray imaging system (information processing system) according to the first embodiment of the present invention. As shown in FIG. 2, the X-ray imaging apparatus 110 is constituted by a control unit 111, a random access memory (RAM) 112, an X-ray sensor interface (IF) 113, an X-ray generator interface (IF) 114, a storage unit 115, an input unit 116, a display unit 117, a network interface card (NIC) 118 and a bus.

The control unit 111 controls the overall operations of the X-ray imaging apparatus 110 by controlling the RAM 112, the X-ray sensor IF 113, the X-ray generator IF 114, the storage unit 115, the input unit 116, the display unit 117 and the NIC 118 by connection via the bus as required.

The control unit 111 controls each constituting unit connected to the bus by transferring control programs stored in the storage unit 115, for example, to the RAM 112 and executing the control programs in the RAM 112.

The RAM 112 is a temporary storage unit for information and is used as a storage region for control programs executed by the control unit 111, a storage region for displayed image data and a memory region used by control programs.

The X-ray sensor IF 113 is an interface configured to connect the X-ray imaging apparatus 110 and the X-ray detection apparatus (X-ray sensor) 130 and acquires digital imagery for use as medical images from the X-ray detection apparatus 130 according to control from the control unit 111.

The X-ray generator IF 114 is an interface configured to connect the X-ray imaging apparatus 110 and the X-ray generator 120 and emits X-rays 123 from the X-ray generator 120 according to control from the control unit 111.

The storage unit 115 is a non-volatile information storage medium formed by a hard-disk drive (HDD) or the like and is used as a storage region of information for completed examination including imagery received from the X-ray detection apparatus 130 or the control programs executed by the control unit 111.

The input unit 116 is an input apparatus used when an operator operates a GUI. The input unit 116, for example, may be formed from a pointing device such as a mouse or touch panel, or a keyboard as required.

The display unit 117 is formed, for example, by a display apparatus such as a liquid crystal display (LCD) or a cathode ray tube (CRT) and displays the GUI or medical images according to the control of the control unit 111.

The NIC 118 is a network interface card configured to enable connection with the hospital local network 160. The control unit 111 communicates with the RIS 140 or the PACS 150 via the NIC 118.

Next, the operation of the X-ray imaging apparatus 110 will be described using an example of an image display by the display unit 117 and a flowchart.

The X-ray imaging apparatus 110 according to the present embodiment is configured to enable parallel execution of processing for a plurality of operations. For example, operations to be executed include examination using X-ray imaging or reference to captured images from previous examinations. New operations are added to the display unit 117 of the X-ray imaging apparatus 110 by display of a new examination button or historical examination reference button as a GUI and an operator presses the relevant button to commence the operation.

Figure 3:
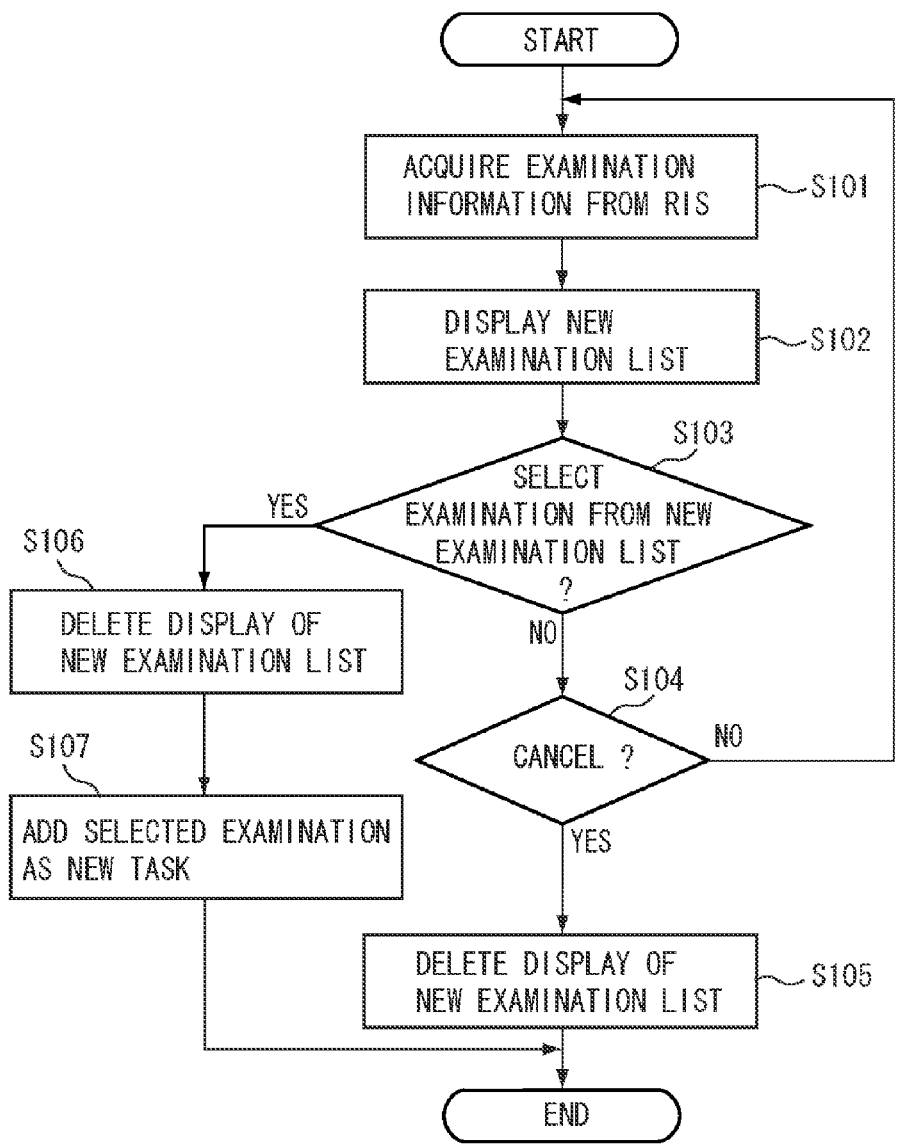
FIG. 3 is a flowchart illustrating an example of the processing sequence when operating a new examination button in an X-ray imaging system (information processing system) according to the first embodiment of the present invention.

FIG. 3 is a flowchart illustrating an example of the processing sequence when operating a new examination button in an X-ray imaging system (information processing system) according to the first embodiment of the present invention.

When the new examination button is pressed by an operator via the input unit 116, firstly in step S101, the control unit 111 of the X-ray imaging apparatus 110 acquires examination information (examination order information) by accessing the RIS 140.

Then in step S102, the control unit 111 of the X-ray imaging apparatus 110 displays the new examination list on the display unit 117.

Figure 4:
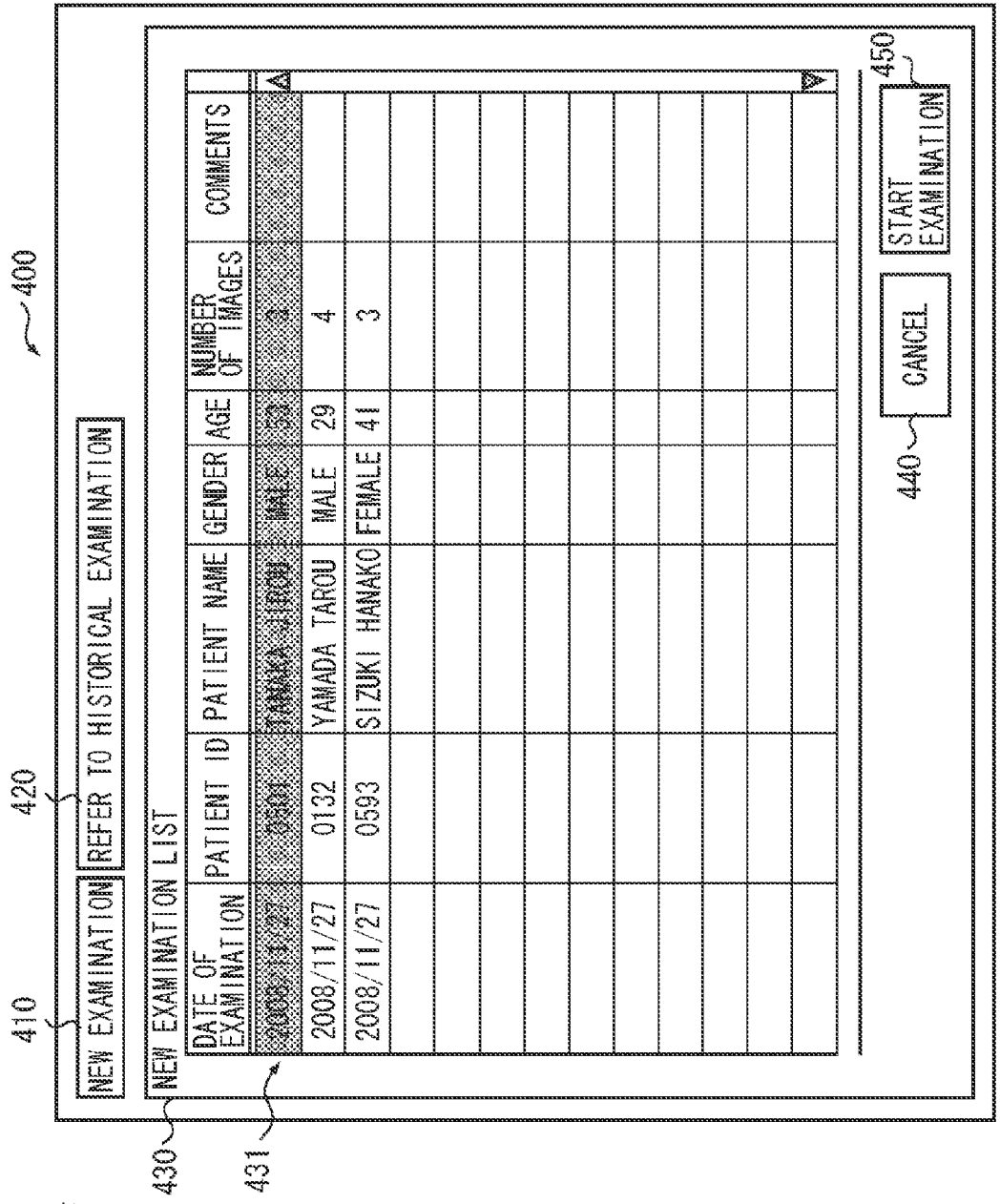
FIG. 4 illustrates the first embodiment of the present invention and is a schematic diagram illustrating an example of a new examination list screen displayed on a display unit in FIG. 2 when the new examination button is pressed.

FIG. 4 illustrates the first embodiment of the present invention and is a schematic diagram illustrating an example of a new examination list screen displayed on a display unit 117 in FIG. 2 when the new examination button is pressed.

A new examination button 410, an historical examination reference button 420, a new examination list 430, a cancel button 440 and an examination start button 450 are arranged on the screen 400 of the new examination list illustrated in FIG. 4.

A new examination is displayed as a single line on the new examination list 430. Examination information including date of examination, patient ID, patient name, gender, age, number of images and comments is displayed for each new examination. An operator selects an examination to be executed from the displayed new examination list 430 and presses the examination start button 450 or finishes the display of the screen 400 of the new examination list by pressing the cancel button 440. When an examination to be executed is selected by the operator from the displayed new examination list 430, the examination is displayed as an object identification frame as illustrated by the examination 431.

The description will now return to FIG. 3. In step S103, the control unit 111 of the X-ray imaging apparatus 110 determines whether or not the examination start button 450 is pressed by an operator to select an examination to be executed from the new examination list 430 displayed on the display unit 117.

When the results of the determination in step S103 indicate that the examination start button 450 has not been pressed to select an examination to be executed from the new examination list 430 (NO in step S103), the process proceeds to step S104.

In step S104, the control unit 111 of the X-ray imaging apparatus 110 determines whether or not the cancel button 440 has been pressed by an operator.

When the results of the determination in step S104 indicate that the cancel button 440 has not been pressed (NO in step S104), the process returns to step S102.

When the results of the determination in step S104 indicate that the cancel button 440 has been pressed (YES in step S104), the process proceeds to step S105.

In step S105, the control unit 111 of the X-ray imaging apparatus 110 deletes the display of the new examination list 430 displayed on the display unit 117 and finishes the process illustrated in the flowchart in FIG. 3.

When the results of the determination in step S103 indicate that the examination start button 450 has been pressed to select an examination to be executed from the new examination list 430 (YES in step S103), the process proceeds to step S106.

In step S106, the control unit 111 of the X-ray imaging apparatus 110 deletes the display of the new examination list 430 displayed on the display unit 117.

Then in step S107, the control unit 111 of the X-ray imaging apparatus 110 adds the examination selected from the new examination list 430 as a new operation and finishes the process illustrated in the flowchart in FIG. 3.

Figure 5:
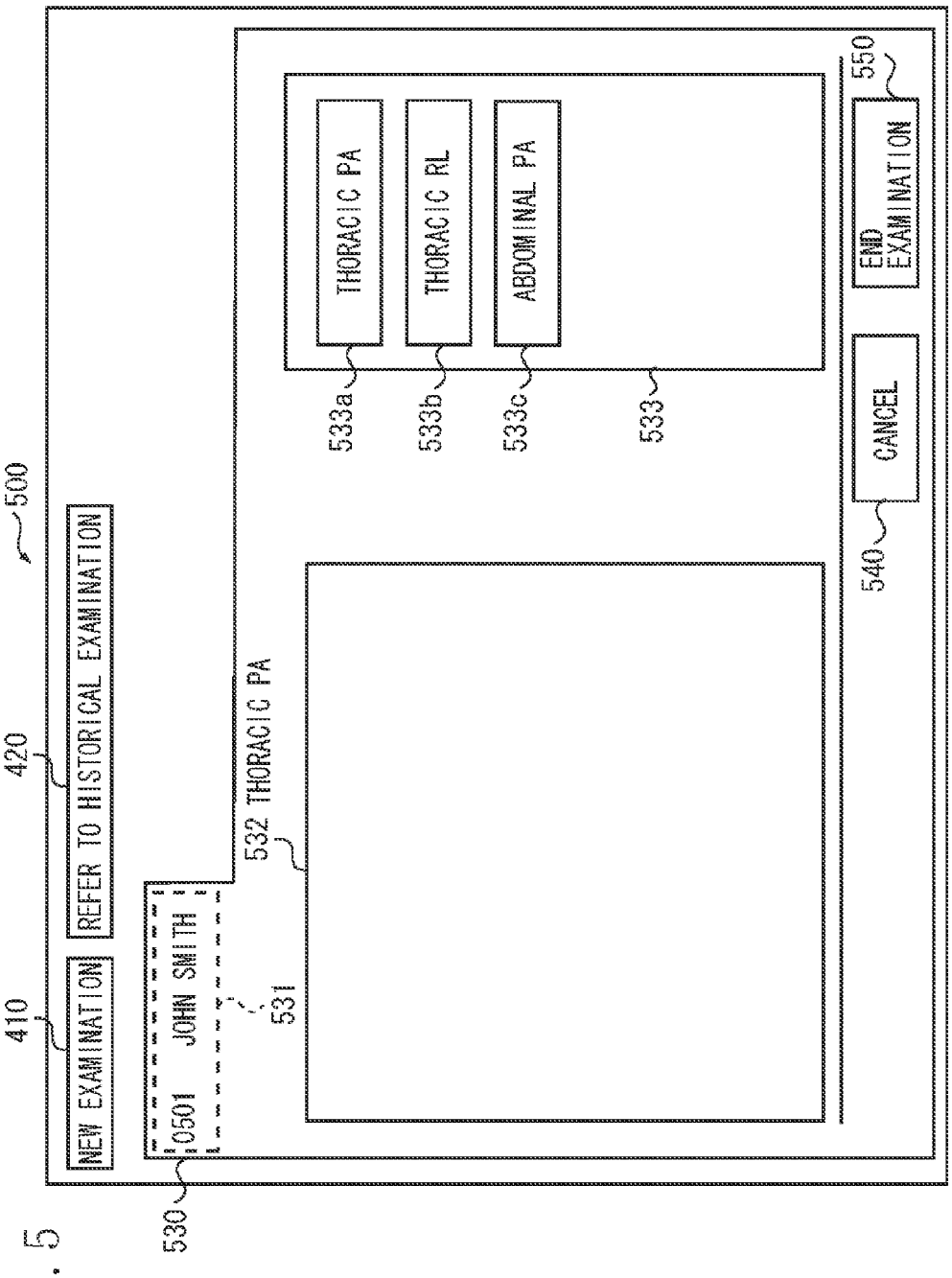
FIG. 5 illustrates the first embodiment of the present invention and is a schematic diagram illustrating an example of an examination screen displayed on a display unit in FIG. 2 when an examination is added as a new operation.

FIG. 5 illustrates the first embodiment of the present invention and is a schematic diagram illustrating an example of an examination screen 117 displayed on a display unit in FIG. 2 when an examination is added as a new operation. In FIG. 5, those functions which are the same as FIG. 4 are denoted by the same reference numerals.

A new examination button 410, an historical examination reference button 420, a new examination content display unit 530, a cancel button 540 and an examination finish button 550 are arranged on the examination screen 500 illustrated in FIG. 5. A tab 531, a medical image display region 532 and an imaging position button display region 533 are arranged on the new examination content display unit 530.

The tab 531 is the display component (header) on the GUI as representative (identifying) of the examination (operation). A patient ID ("0501" in FIG. 5) and a patient name ("John Smith" in FIG. 5) are displayed on the tab 531 to identify the examination.

The medical image display region 532 is a large quadrilateral region below the tab 531 and displays the medical image of the imaged patient.

The imaging position button display region 533 is arranged on the right side of the medical image display region 532 and displays an imaging position buttons (533a-533c) indicating the imaging position of the patient to be imaged. The imaging sequence is shown in the imaging position button display region 533 in order of the imaging positions beginning at the top. The example of the imaging position button display region 533 illustrated in FIG. 5 shows the scheduled imaging order of the total of the three images of the "thoracic PA", "thoracic RL" and "abdominal PA" by the display of each imaging position button (533a-533c).

The cancel button 540 is a button which an operator operates when canceling the examination screen 500. The examination finish button 550 is a button which an operator operates when finishing the examination.

Next the operation process when an operator operates the historical examination reference button will be described.

Figure 6:
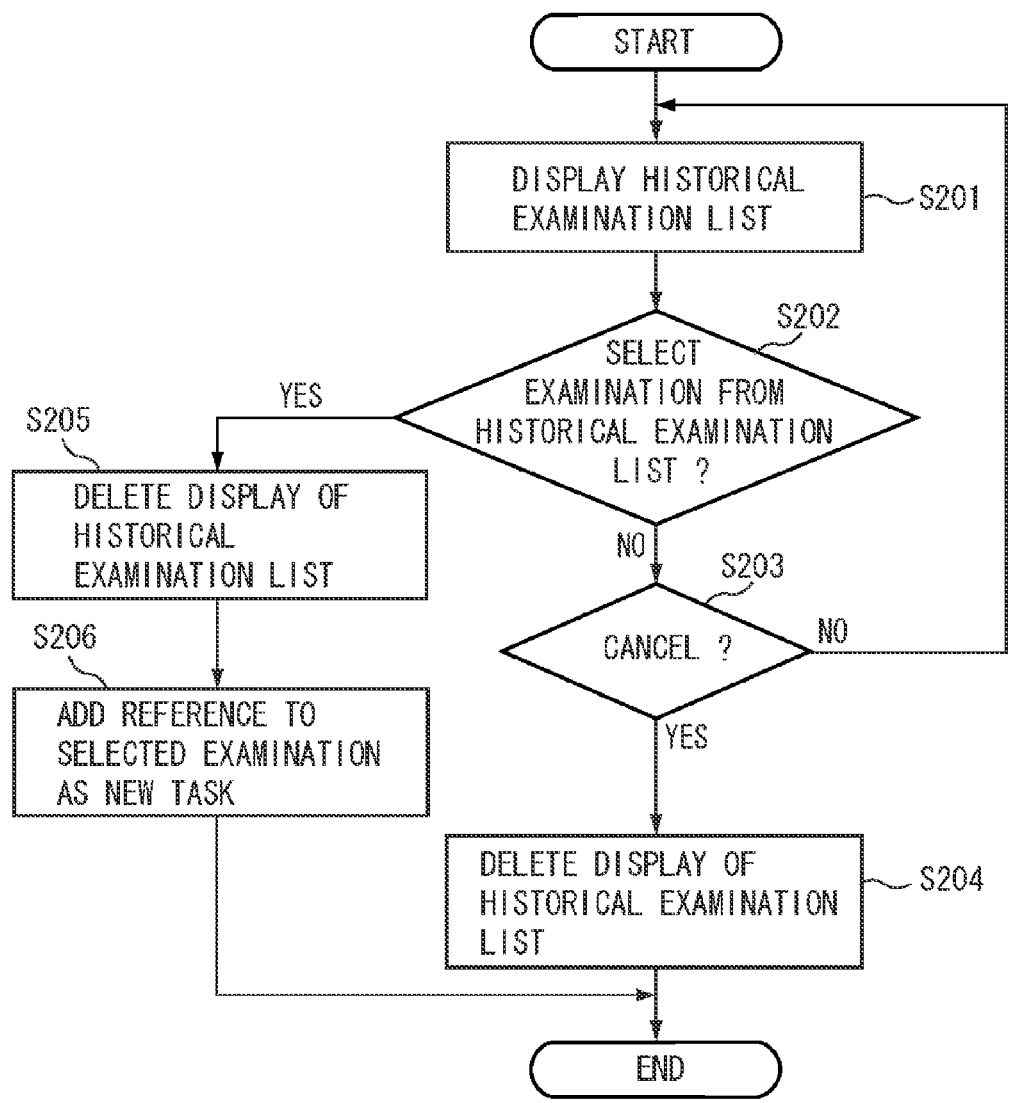
FIG. 6 is a flowchart illustrating an example of the processing sequence when operating an historical examination reference button in an X-ray imaging system (information processing system) according to the first embodiment of the present invention.

FIG. 6 is a flowchart illustrating an example of the processing sequence when historical examination reference button is operated in an X-ray imaging system (information processing system) according to the first embodiment of the present invention.

When the historical examination reference button is pressed by an operator using the input unit 116, firstly in step S201, the control unit 111 of the X-ray imaging apparatus 110 displays an historical examination list on the display unit 117.

Figure 7:
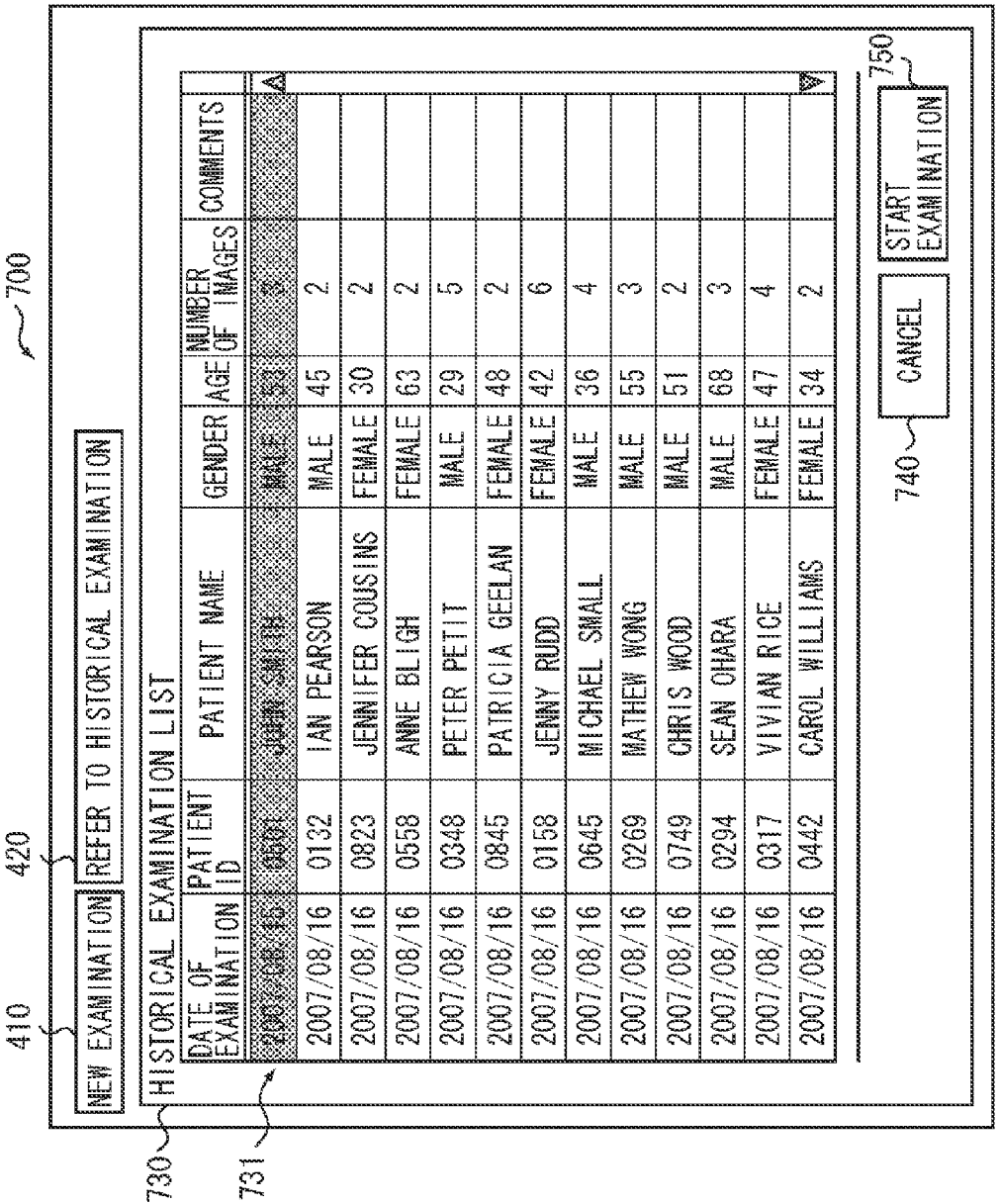
FIG. 7 illustrates the first embodiment of the present invention and is a schematic diagram illustrating an example of a historical examination list screen displayed on a display unit in FIG. 2 when the historical examination reference button is pressed.

FIG. 7 illustrates the first embodiment of the present invention and is a schematic diagram illustrating an example of a historical examination list screen displayed on a display unit 117 in FIG. 2 when the historical examination reference button is pressed. In FIG. 7, those functions which are the same as FIG. 4 are denoted by the same reference numerals.

A new examination button 410, an historical examination reference button 420, an historical examination list 730, a cancel button 740 and a reference button 750 are arranged on the historical examination list screen 700 illustrated in FIG. 7.

An historical examination is displayed as a single line on the historical examination list 730. Examination information including date of examination, patient ID, patient name, gender, age, number of images and comments is displayed for each historical examination. An operator selects an examination to be referenced from the displayed historical examination list 730 and presses the examination start button 750 or finishes the display of the screen 700 of the historical examination list by pressing the cancel button 740. When an examination to be referenced is selected by the operator from the displayed historical examination list 730, the examination is displayed as an object identification frame as illustrated by the examination 731.

The description will return to FIG. 6. Then in step S202, the control unit 111 of the X-ray imaging apparatus 110 determines whether or not the reference button 750 has been pressed by an operator to select an examination to be referenced from the historical examination list 730 displayed on the display unit 117.

When the results of the determination in step S202 indicate that the reference button 750 has not been pressed to select an examination to be referenced from the historical examination list 730 (NO in step S202), the process proceeds to step S203.

In step S203, the control unit 111 of the X-ray imaging apparatus 110 determines whether or not the cancel button 740 has been pressed by an operator.

When the results of the determination in step S203 indicate that the cancel button 740 has not been pressed (NO in step S203), the process returns to step S201.

When the results of the determination in step S203 indicate that the cancel button 740 has been pressed (YES in step S203), the process proceeds to step S204.

In step S204, the control unit 111 of the X-ray imaging apparatus 110 deletes the display of the historical examination list 730 displayed on the display unit 117 and finishes the process illustrated in the flowchart in FIG. 6.

When the results of the determination in step S202 indicate that the reference button 750 has been pressed to select an examination to be referenced from the historical examination list 730 (YES in step S202), the process proceeds to step S205.

In step S205, the control unit 111 of the X-ray imaging apparatus 110 deletes the display of the historical examination list 730 displayed on the display unit 117.

Then in step S206, the control unit 111 of the X-ray imaging apparatus 110 adds the reference of the examination selected from the historical examination list 730 as a new operation and finishes the process illustrated in the flowchart in FIG. 6.

Figure 8:
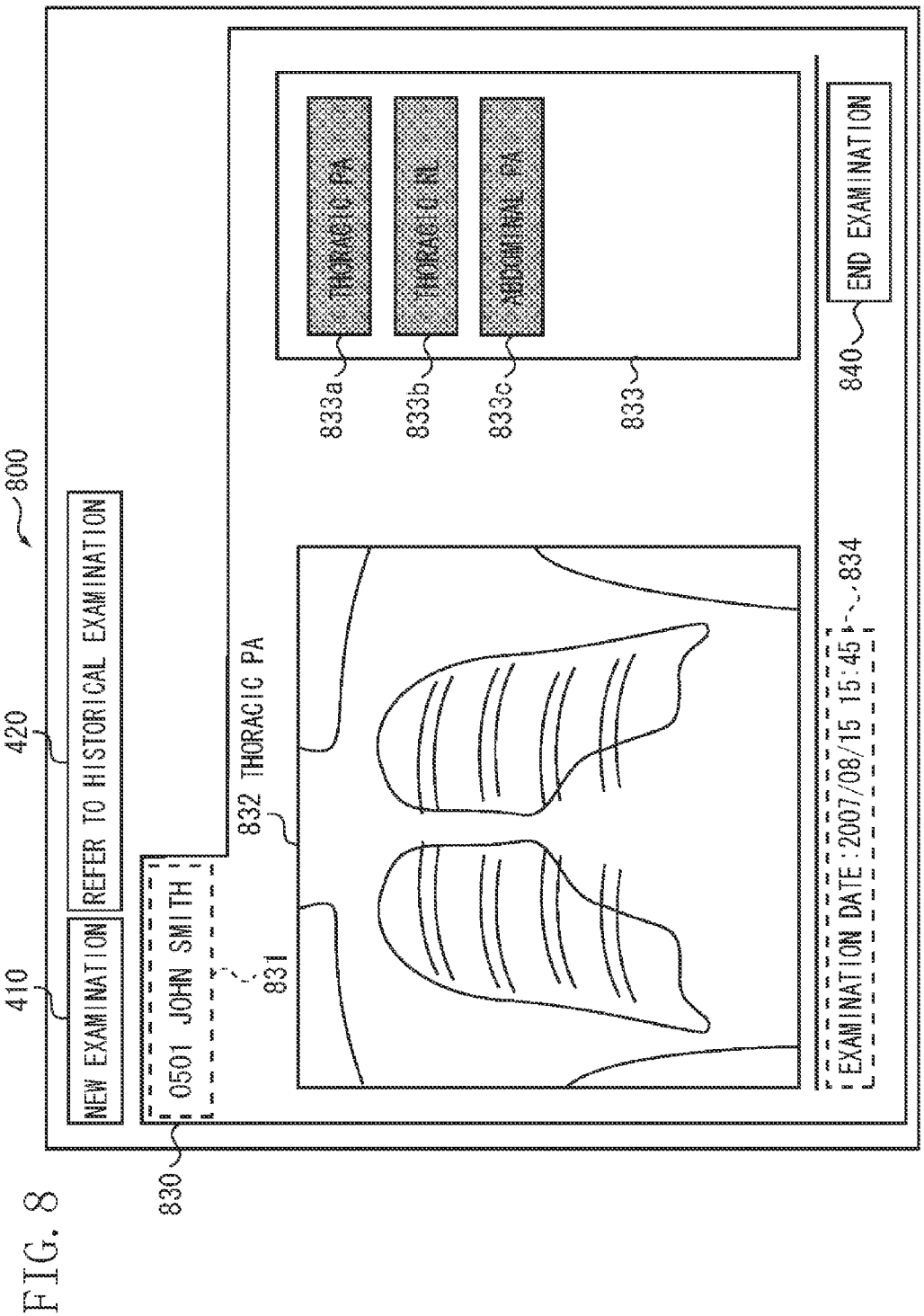
FIG. 8 illustrates the first embodiment of the present invention and is a schematic diagram illustrating an example of an examination screen displayed on a display unit in FIG. 2 when an examination reference is added as a new operation.

FIG. 8 illustrates the first embodiment of the present invention and is a schematic diagram illustrating an example of an examination screen 117 displayed on a display unit in FIG. 2 when a reference for an examination is added as a new operation. In FIG. 8, those functions which are the same as FIG. 4 are denoted by the same reference numerals.

A new examination button 410, an historical examination reference button 420, an historical examination content display unit 830 and a reference finish button 840 are arranged on the examination screen 800 illustrated in FIG. 8. A tab 831, a medical image display region 832, an imaging position button display region 833 and examination time and date display region 834 are arranged on the historical examination content display unit 830.

The tab 831 displays a patient ID ("0501" in FIG. 8) and a patient name ("John Smith" in FIG. 8) to identify the examination in the same manner as the examination screen 500 illustrated in FIG. 5.

When the imaging position buttons (833a-833c) in the imaging position button display region 833 are selected, a medical image for the imaging position corresponding to the selected imaging position button is displayed on the medical image display region 832. The example illustrated in FIG. 8 shows a total of the three images of the "thoracic PA", "thoracic RL" and "abdominal PA" imaged in that order in the historical examination of the patient.

Examination date and time information indicating when the medical image displayed on the medical image display region 832 has been taken is displayed on the date and time display region 834.

When the reference finish button 840 is pressed, the display of the reference screen 800 is deleted and the reference operation is finished.

Figure 9:
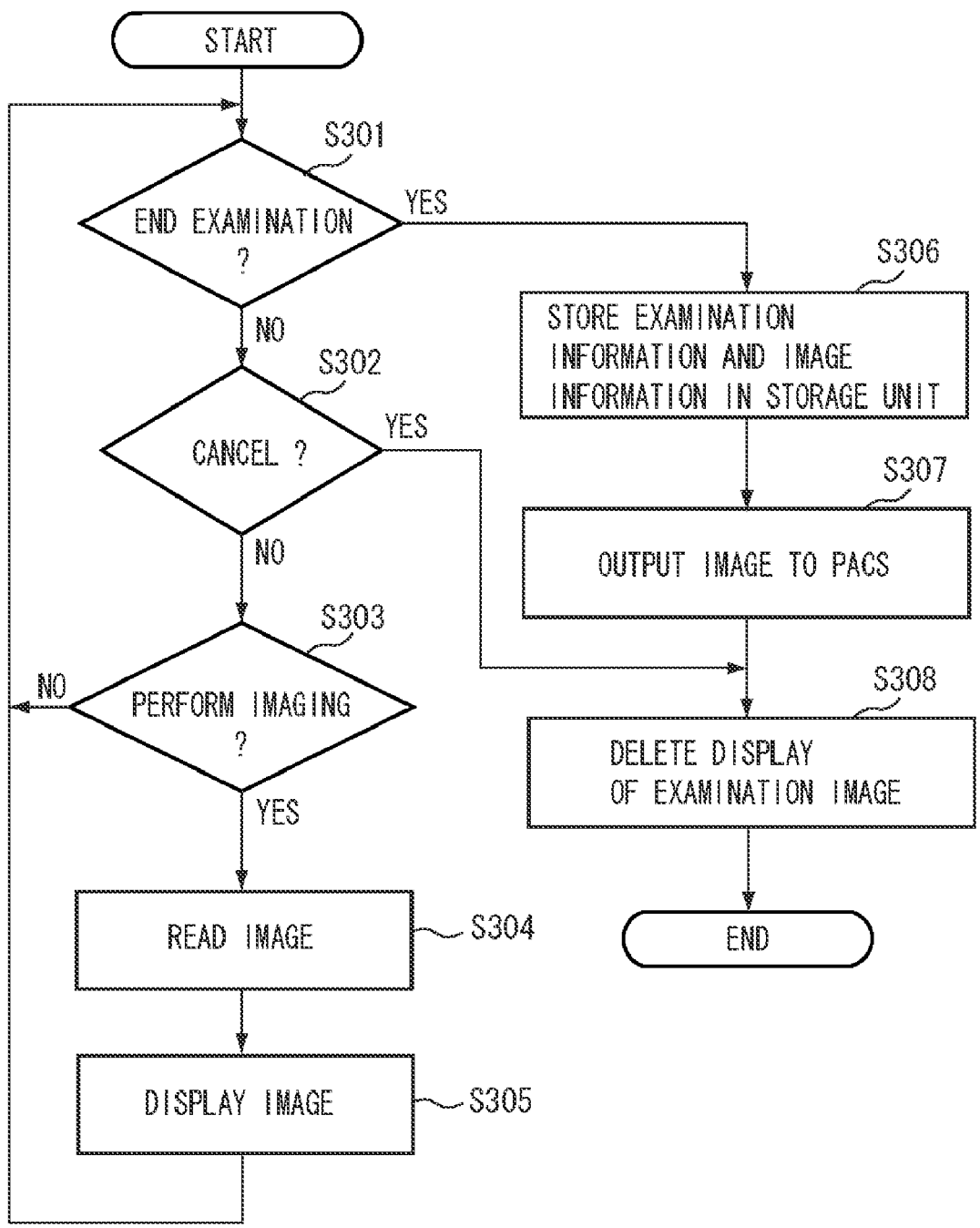
FIG. 9 is a flowchart illustrating an example of the processing sequence when operating the examination screen as illustrated in FIG. 5 in an X-ray imaging system (information processing system) according to the first embodiment of the present invention.

The process corresponding to an operation of the examination screen 500 illustrated in FIG. 5 will now be described. FIG. 9 is a flowchart illustrating an example of the processing sequence when operating an examination screen 500 as illustrated in FIG. 5 in an X-ray imaging system (information processing system) according to the first embodiment of the present invention.

FIG. 5 illustrates an examination screen 500 when commencing an examination operation. Processes for the examination screen 500 include the examination finish process executed by pressing the examination finish button 550, the cancel process executed by pressing the cancel button 540 and the imaging process for the X-ray imaging (medical imaging). A screen is switched to the examination screen 500 in FIG. 5 when the examination commencement button 450 is pressed on the screen 400 for the new examination list illustrated in FIG. 4. Therefore, the imaging process of X-ray images, for example, is executed when the cancel button 540 and the examination finish button 550 are not pressed. An imaging process for an X-ray image (medical image) may also be performed when an examination commencement button is newly formed on the examination screen 500 illustrated in FIG. 5 and the examination commencement button is pressed.

Firstly in step S301 in FIG. 9, the control unit 111 of the X-ray imaging apparatus 110 determines whether or not the examination finish button 550 is pressed by an operator.

When the results of the determination in step S301 indicate that the examination finish button 550 has not been pressed (NO in step S301), the process proceeds to step S302.

In step S302, the control unit 111 of the X-ray imaging apparatus 110 determines whether or not the cancel button 540 has been pressed by an operator.

When the results of the determination in step S302 indicate that the cancel button 540 has not been pressed (NO in step S302), the process proceeds to step S303.

In step S303, the control unit 111 of the X-ray imaging apparatus 110 determines whether or not to perform imaging of an X-ray image (medical image).

When the results of the determination in step S303 indicate that imaging of an X-ray image (medical image) is not performed (NO in step S303), the process returns to step S301.

On the other hand, when the results of the determination in step S303 indicate that imaging of an X-ray image (medical image) is performed (YES in step S303), the process proceeds to step S304.

In step S304, the control unit 111 of the X-ray imaging apparatus 110 controls the X-ray generator 120 and the X-ray detection apparatus 130 to execute an X-ray imaging examination of the patient 200 and reads the digital image from the X-ray detection apparatus 130.

Then in step S305, the control unit 111 of the X-ray imaging apparatus 110 executes the required image processing for the digital image read in step S304 and then displays the image as a medical image on the display unit 117.

Figure 10:
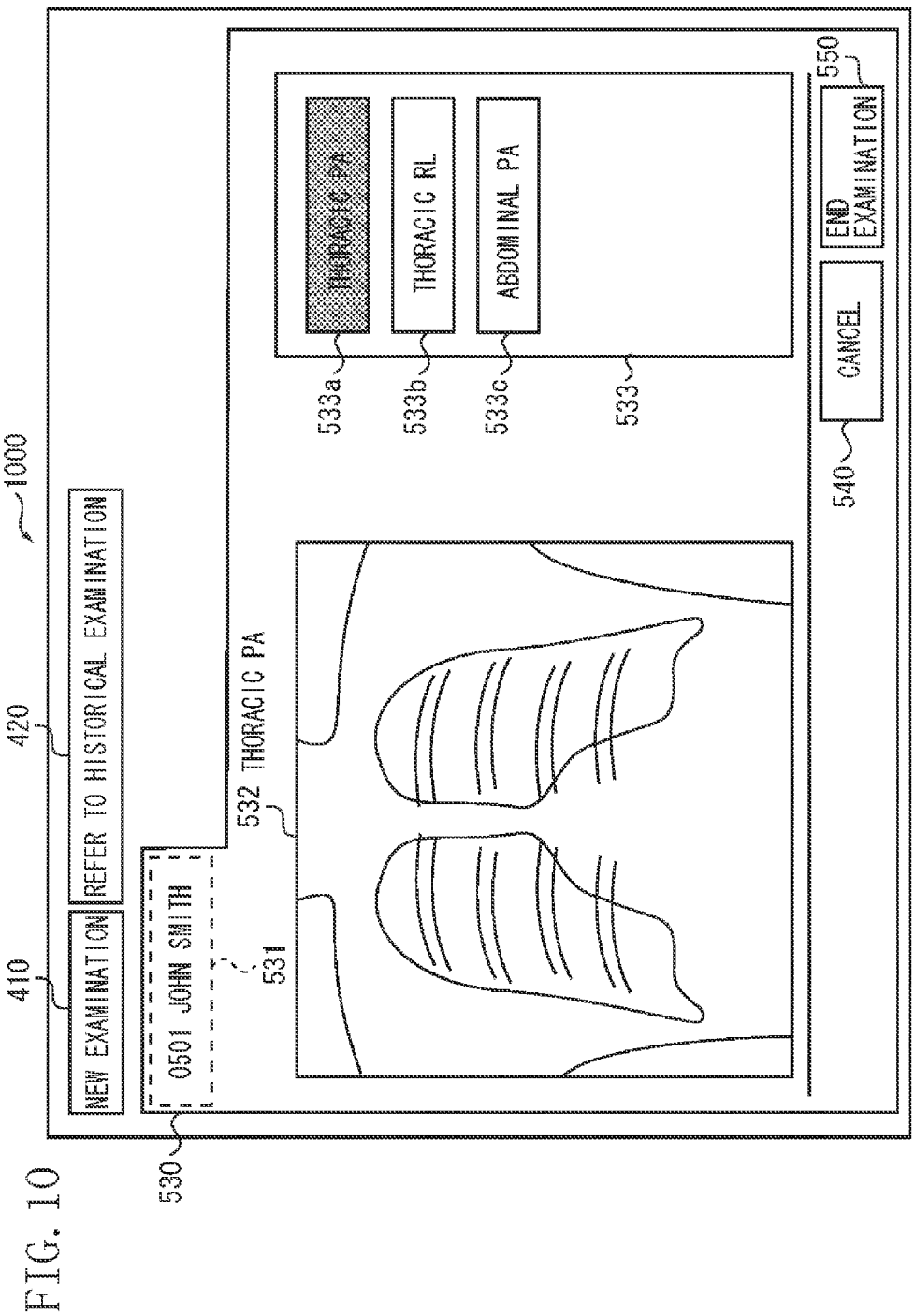
FIG. 10 illustrates the first embodiment of the present invention and is a schematic diagram illustrating an example of an examination screen when capturing a medical image in the state of the examination screen illustrated in FIG. 5.

FIG. 10 illustrates the first embodiment of the present invention and is a schematic diagram illustrating an example of an examination screen when capturing a medical image in the state of the examination screen 500 illustrated in FIG. 5. In FIG. 10, those functions which are the same as FIG. 5 are denoted by the same reference numerals.

In the examination screen 1000 illustrated in FIG. 10, a medical image obtained by the imaging process is displayed on the medical image display region 532. The button for the currently imaged position (more specifically, the imaging position button 533a) among the buttons for the scheduled imaging position (533a-533c) is displayed in the imaging position button display region 533 in a color changed to indicate completion of imaging.

When the process in step S305 in FIG. 9 is completed, the process returns to step S301.

When the results of the determination in step S301 indicate that the examination finish button 550 has been pressed (YES in step S301), the process proceeds to step S306.

In step S306, the control unit 111 of the X-ray imaging apparatus 110 stores information for the captured medical image and examination information (examination order information) received from the RIS 140 in the storage unit 115 as information relating to the examination.

Then in step S307, the control unit 111 of the X-ray imaging apparatus 110 transfers the medical image obtained by the X-ray imaging to the PACS 150.

When the process in step S307 is finished or when it is determined that the cancel button 540 in step S302 has been pressed (YES in step S302), the process proceeds to step S308.

In step S308, the control unit 111 of the X-ray imaging apparatus 110 deletes the display of the examination screen displayed on the display unit 117 and completes the process of the flowchart illustrated in FIG. 9.

The X-ray imaging apparatus 110 according to the present embodiment is configured to enable completion of the examination operation even when all scheduled imaging of imaging positions has not been completed, or addition of imaging operations at the discretion of an operator after completion of all imaging at the imaging position.

Normally when a new examination is commenced, a task in the apparatus is dedicated to that operation until completion thereof. However, sometimes, a more urgent examination must be executed in priority to the currently executed examination. Since a plurality of operations can be executed in parallel in the X-ray imaging apparatus 110 according to the present embodiment, such a demand can be dealt with.

In the examination screen illustrated in FIG. 10 as described above, an examination is being carried out and single imaging of a patient (more specifically, a ID "0501" and a patient name "john smith") has been completed. Since the number of images of the patient is three as shown by the imaging position button (533a-533c), and two more images remain. However, according to the present embodiment, an examination of another patient with higher priority can be performed without stopping the examination of the current patient.

More specifically, an operator presses the new examination button 410 without finishing the current examination operation and selects the next examination from the new examination list (the new examination list 430 illustrated in FIG. 4) with the same operation as that used to commence a normal examination operation.

Figure 11:
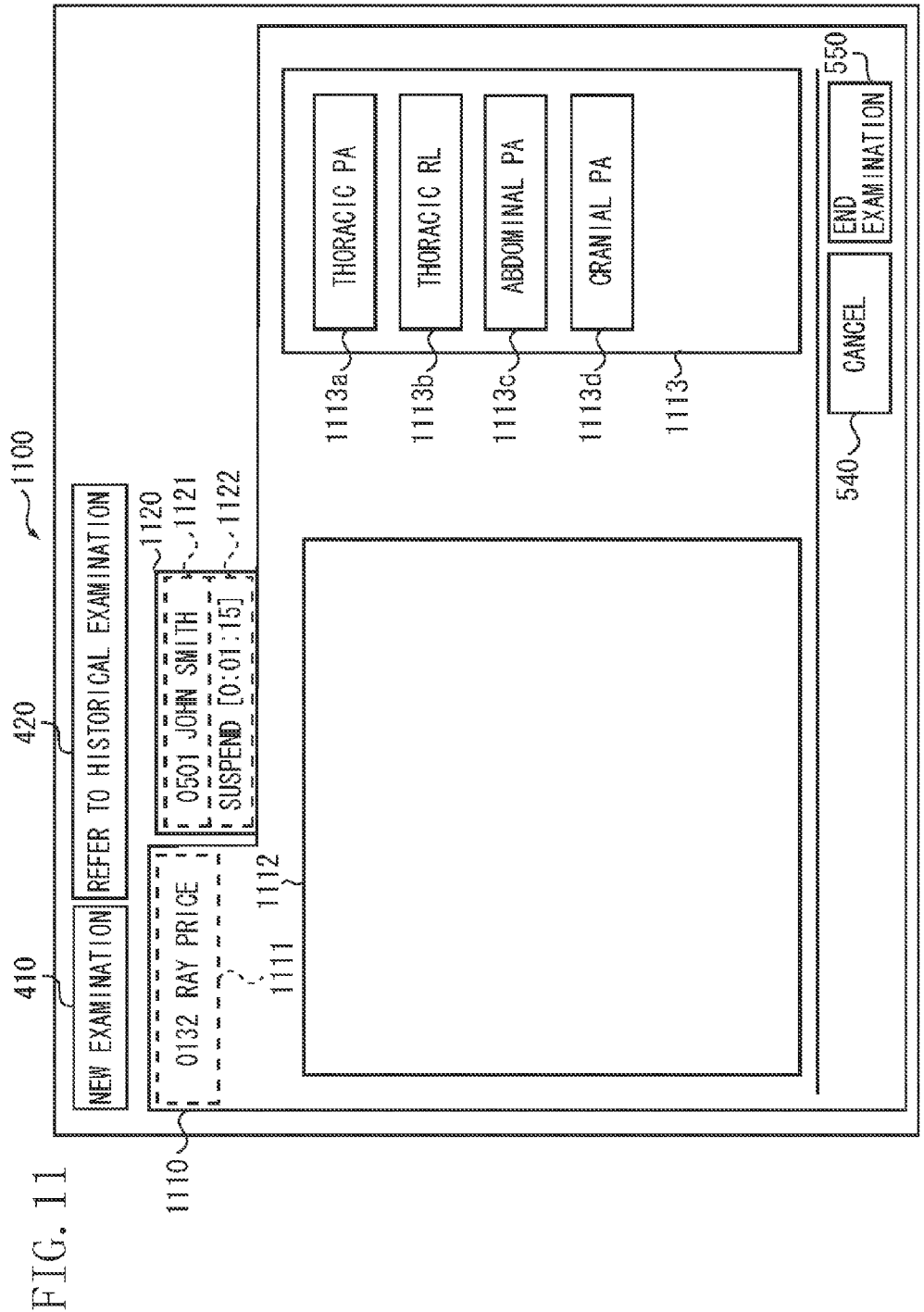
FIG. 11 illustrates the first embodiment of the present invention and is a schematic diagram illustrating an example of an examination screen displayed on the display unit in FIG. 2 when adding an examination of a new patient as a new operation in the state of the examination screen illustrated in FIG. 10.

FIG. 11 illustrates the first embodiment of the present invention and is a schematic diagram illustrating an example of an examination screen 1000 displayed on the display unit 117 in FIG. 2 when adding an examination of a new patient as a new operation in the state of the examination screen 117 illustrated in FIG. 10. In FIG. 11, those functions which are the same as FIG. 5 are denoted by the same reference numerals.

In the examination screen 1100 illustrated in FIG. 11, the tab 1111 is related to the current operation and displays the new examination contents in the new examination contents display unit 1110. In the examination screen 1100 illustrated in FIG. 11, the examination illustrated in FIG. 10 which has been previously executed is placed in a state of suspension and displayed on the display unit 117 on the GUI as a tab 1120 for a non-selected state.

More specifically, the control unit 111 controls the display on the suspended examination tab 1120 containing information for the patient ID and the patient name ("0501 John Smith" in FIG. 11) 1121 and suspension information 1122 indicating that such information is suspended. In the present embodiment, when an examination operation is suspended, operations are stopped in the state at which the suspension became effective. In other words, the state when the suspension is applied or when the task executing a process in the flowchart in FIG. 9 is stopped is retained and the tasks for the newly added examination operation are executed separately according to the processing of the flowchart in FIG. 9.

Suspension information 1122 will be described hereafter. A suspension time which is the time elapsing since the application of the suspension (the time from the removal of the focus in the current operation) is displayed as suspension information 1122. More specifically, in the example illustrated in FIG. 11, the suspension time is shown as suspension information 1122 in the form of [0:03:26] to indicate a state of "suspension".

FIG. 12 is a schematic diagram illustrating an example of a suspension information table managed by an X-ray imaging system (information processing system) according to the first embodiment of the present invention. The suspension information for display on each tab is recorded in the suspension information table illustrated in FIG. 12 and, for example, is stored and managed in the storage unit 115 illustrated in FIG. 2.

The suspension information table illustrated in FIG. 12 manages the suspension time and the tab for the current operation. More specifically, the tab for the current operation is displayed as a current tab [1] as illustrated in FIG. 12. Other suspended tabs are shown as current tabs [0] as illustrated in FIG. 12. In other words, the suspended tabs are displayed as the current tabs [0] illustrated in FIG. 12. The suspension information (suspension time) of the suspended tabs, for example, is a time measured by the control unit 111 and is managed and stored periodically in the storage unit 115. The control unit 111 measuring the suspension time forms a time measuring unit. In the present example, although the control unit 111 measures the suspension time, for example, a time measurement unit may also be provided separately as an inner component of the X-ray imaging apparatus 110 illustrated in FIG. 2 and the time measurement unit may be configured to measure the suspension time according to the control of the control unit 111.

The tab for the current operation, in other words, the suspend information (suspension time) is a current tab [1] in FIG. 12 and shows [0:00:00] since the tab does not indicate suspension. Furthermore in the present embodiment, the display of the suspension information 1122 is performed periodically as a separate task to the task of executing the examination operation.

More specifically, the suspension information table illustrated in FIG. 12 is suitably varied, for example, by the control unit 111 when a tab is added, deleted or, an operator switches the current operation.

For example, when a tab is added, the control unit 111 displays the new tab on the display unit 117. Furthermore the control unit 111 adds a line corresponding to the tab in the suspension information table illustrated in FIG. 12, stores [0:00:00] as suspension information and varies the current tab information to [1] so that that tab becomes current. At this time, the control unit 111 commences measurement of time according to suspended tab.

Figure 13:
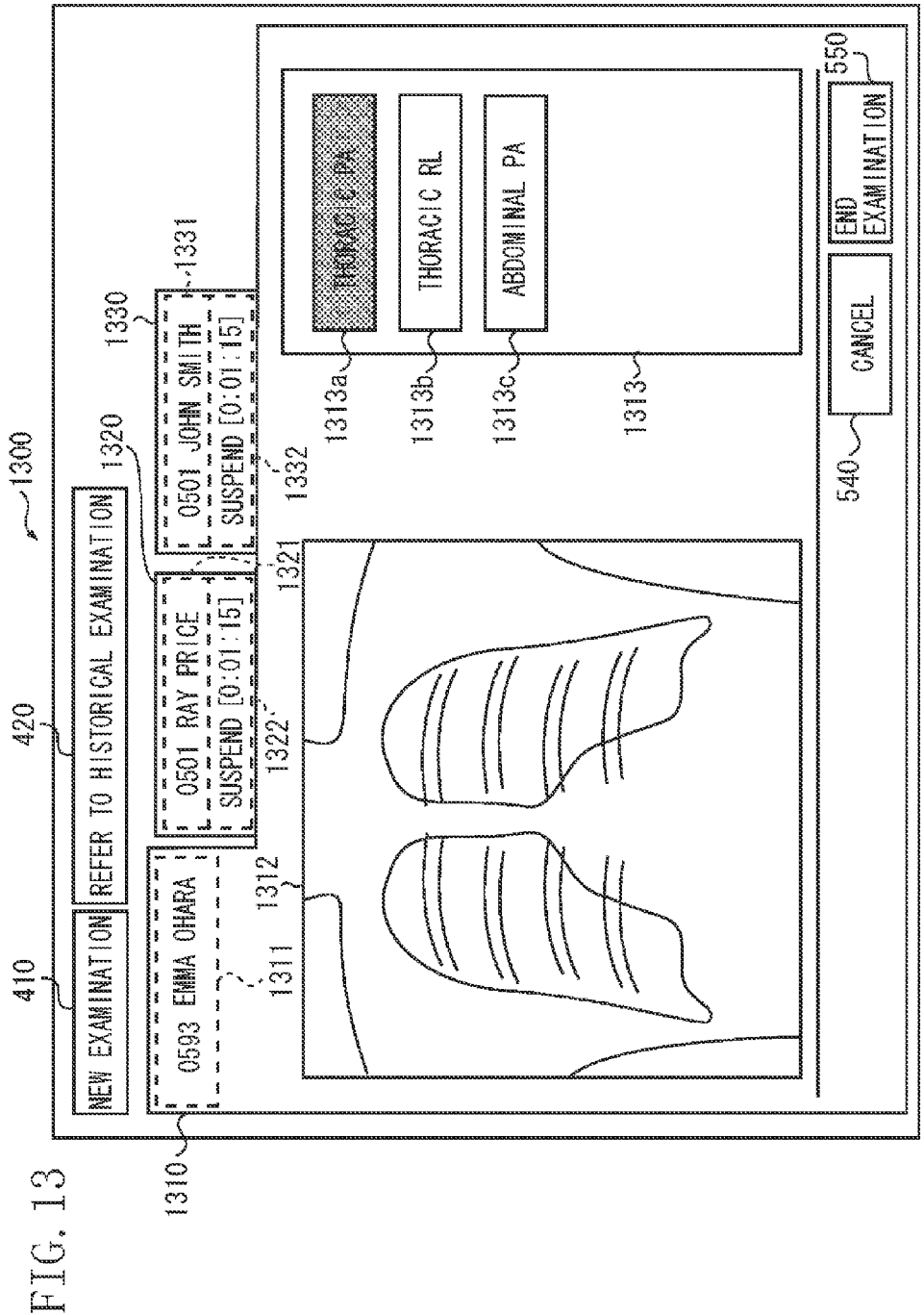
FIG. 13 illustrates the first embodiment of the present invention and is a schematic diagram illustrating an example of an examination screen displayed when adding an examination of a new patient as a new operation and capturing a medical image in the state of the examination screen illustrated in FIG. 11.

FIG. 13 illustrates the first embodiment of the present invention and is a schematic diagram illustrating an example of an examination screen displayed when adding an examination of a new patient as a new operation and capturing a medical image in the state of the examination screen 1100 illustrated in FIG. 11.

In the examination screen 1300 illustrated in FIG. 13, the tabs for the current operation are the tabs 1311 and the new examination contents are displayed in the new examination content display unit 1310. The examination screen 1300 illustrated in FIG. 13 shows the situation in which the suspended operations are two operations on the tab 1320 and on the tab 1330. Information for the patient ID and patient name 1321 and 1331 and suspension information 1322 and 1332 showing the suspension state, are displayed in each tab 1320 and 1330.

More specifically, the operation on the tab 1320 in FIG. 13 corresponds to the operation on the tab 1111 illustrated in FIG. 11, the operation on the tab 1330 in FIG. 13 corresponds to the operation on the tab 1120 illustrated in FIG. 11 and the respective suspension times in the suspension information 1322 and 1332 are varied. More specifically, the operation on the tab 1320 has a suspension time of 1 min. 15 sec and the operation on the tab 1330 has a suspension time of 5 min. 41 sec.

When the control unit 111 finishes the current operation (in the example illustrated in FIG. 13, the operation on the tab 1311) and deletes the display of that tab, a deletion process is applied to the corresponding line in the suspension time table illustrated in FIG. 12. For example, the control unit 111 searches the suspension information for a tab having the shortest suspension time, updates the suspension information table illustrated in FIG. 12 so that that tab becomes the current tab and controls the display by updating the examination screen on the display unit 117. At this time, the suspension information of the tab of the current operation is reset to [0:00:00] and the suspension information table in FIG. 12 is updated.

In the present embodiment, control is performed by the above process to return automatically to an operation executed immediately prior to the currently executed current operation. For example, when an operator presses the examination finish button 550 to finish the operation (operation for the tab 1311) of the current examination while the examination screen 1300 is in the state shown in FIG. 13, the examination screen 1100 illustrated in FIG. 11 enables selection of the tab. However, the displayed suspension information for the suspended tabs is the suspension time at that point.

When the operator selects a suspended tab and changes the current operation, the control unit 111, for example, updates the display of the display unit 117. At the same time, the control unit 111, for example, updates the information of the current tab of the suspension information table illustrated in FIG. 12, resets the suspension information of the newly current tab to [0:00:00] and commences measurement of the suspension time according to the suspended tab. For example, in the examination screen 1300 in FIG. 13, when an operator selects the tab 1320 which is the second from the left end, the state as illustrated by the examination screen 1400 in FIG. 14 is obtained.

Figure 14:
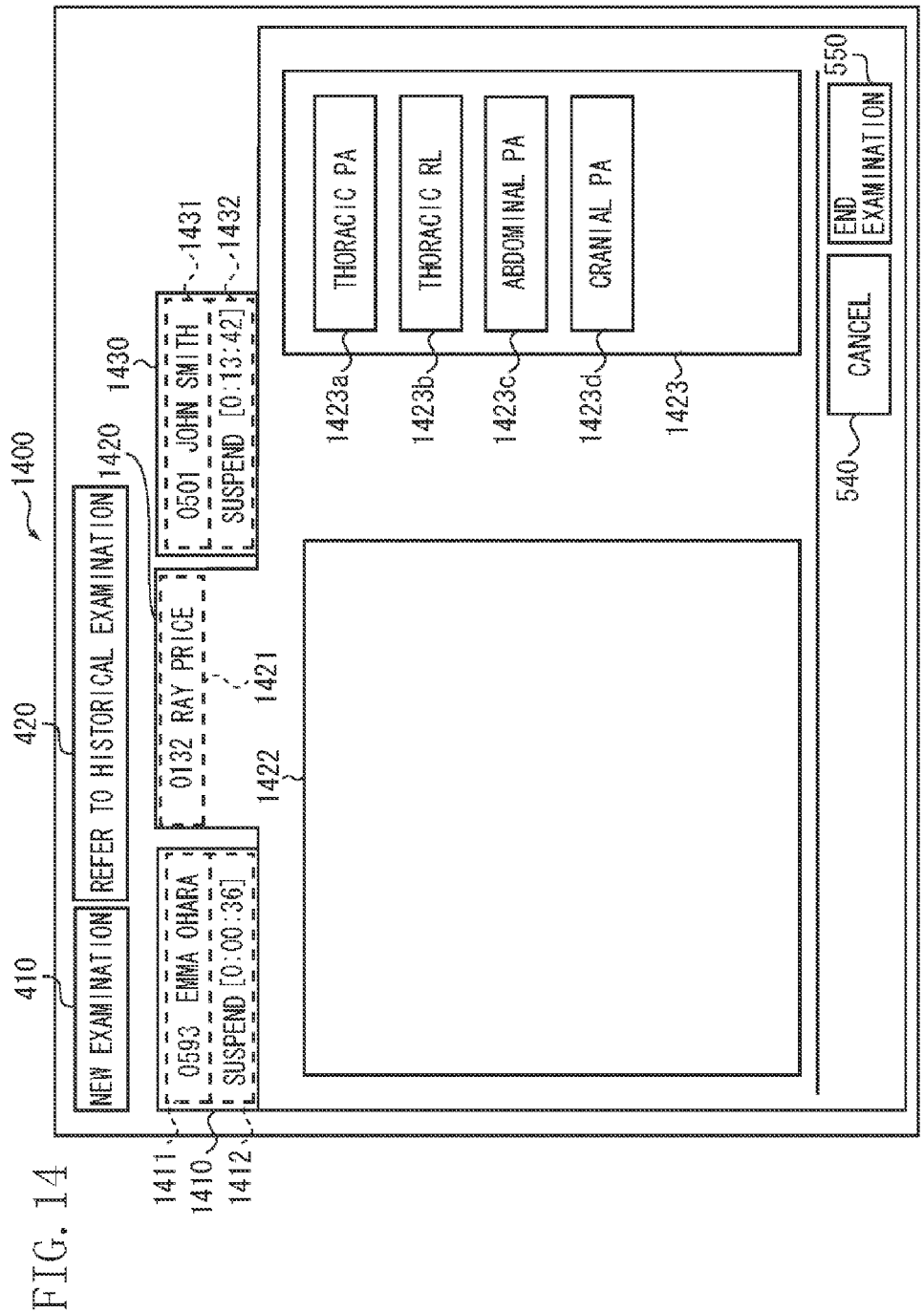
FIG. 14 illustrates the first embodiment of the present invention and is a schematic diagram illustrating an example of an examination screen when selecting the second tab from the left end, in the state of the examination screen illustrated in FIG. 13.

FIG. 14 illustrates the first embodiment of the present invention and is a schematic diagram illustrating an example of an examination screen when selecting the second tab 1320 from the left end in the state of the examination screen 1300 illustrated in FIG. 13. More specifically, the operation on the tab 1410 in FIG. 14 corresponds to the operation on the tab 1311 illustrated in FIG. 13, the operation on the tab 1421 in FIG. 14 corresponds to the operation on the tab 1320 illustrated in FIG. 13 and the operation on the tab 1430 in FIG. 14 corresponds to the operation on the tab 1330 illustrated in FIG. 13.

In the examination screen illustrated in FIG. 14 as described above, the tab 1421 is related to the current operation and the new examination contents are shown in the new examination content display unit 1420. In the examination screen illustrated in FIG. 14, information 1411 and 1431 for the patient ID and the patient name and the suspension information 1412 and 1432 displaying the suspension state are displayed in each tab 1410 and 1430 which are the tabs for suspended operations.

Generally, when adding a new operation, an operator adds an operation with a higher priority than the currently executed operation. However in a conventional technique, for example, when the added operations are increased, it is not possible to decide how long to delay a suspended operation and thus there is the possibility that a suspended operation will remain overlooked. In this case, when the suspension time for the suspended operation is long, it may be preferable to execute the suspended operation without adding a new operation.

The X-ray imaging apparatus 110 in the present embodiment firstly displays a tab (header) identifying each operation, for a plurality of operations on the display unit 117. The control unit 111 is configured to switch the current operation using the tab selected via the input unit 116. When switching the current operation, the control unit 111 displays the suspension information (suspension time etc.) illustrating the suspension state of the suspended operations. In this manner, the operator can understand how long a suspended operation has been suspended. Thus, the present embodiment prevents a suspended operation from being overlooked. In particular, as shown by the present embodiment, when applying the information processing system of the present invention to an X-ray imaging system, waiting time of a patient can be prevented from becoming unnecessarily long.

In the present embodiment, a time period measured starting from releasing the focus of the current operation is used as an example of suspension information. However, the time measured from the first releasing of the focus of the current operation can also be used as suspension information. Furthermore, a time period calculated by accumulating all suspended time periods can also be applied as suspension information. In this case, the same effect is obtained as that when applying a time period measured from the time of releasing the focus of the current operation as suspension information.

A second embodiment of the present invention will be described hereafter. The schematic structure of the X-ray imaging system according to the second embodiment is the same as the schematic structure of the X-ray imaging system 100 according to the first embodiment illustrated in FIG. 1. The internal structure of the X-ray imaging apparatus according to the second embodiment is the same as the internal structure of the X-ray imaging system 110 according to the first embodiment illustrated in FIG. 2. Furthermore, a system for adding a new examination operation in the second embodiment, a system for adding an historical examination reference operation and a process in the flowchart from commencement to completion of the examination operation according to the second embodiment are the same as the first embodiment.

The two operations performed in the X-ray imaging system 100 are the examination operation and the historical examination reference operation as described in the first embodiment. When an examination operation is suspended, the patient in that examination must wait until the suspension is removed. On the other hand, a reference operation for an historical examination is executed for the purpose of an operation referring to an historical image and there is no necessity for the patient to wait even in the event that operation is suspended. When the operation is suspended or remains uncompleted, this type of operation does not create a large problem since it is a task which exists only inside the X-ray imaging system 100.

When the suspension information is displayed for all suspended operations, it is difficult to distinguish between operations which should not remain uncompleted and operation which may remain uncompleted. Thus in the second embodiment, depending on the contents of the operation, suspension information are not displayed during a period of suspension with respect to operations which may remain uncompleted without problem even if suspended.

FIG. 15 is a schematic diagram illustrating an example of a suspension information table managed by an X-ray imaging system (information processing system) according to the second embodiment of the present invention. In the suspension information table illustrated in FIG. 15, the difference from the suspension information table illustrated in FIG. 12 used in the first embodiment is the addition of a suspension information display flag. Whether the suspension information is to be displayed or not is determined by the suspension information flag if the tag is suspension.

If the suspension information display flag of the suspension information table illustrated in FIG. 15 is [1] and the current tab is [0], it is a display target of suspension information. In the present embodiment, when adding a new tab to the suspension information table illustrated in FIG. 15, the control unit 111 determines the value of the suspension information display flag using the contents of the operation items for that tab. In the present embodiment, the control unit 111 sets the suspension information display flag to [1] for examination operations and sets the suspension information display flag to [0] for historical examination reference operations.

Figure 16:
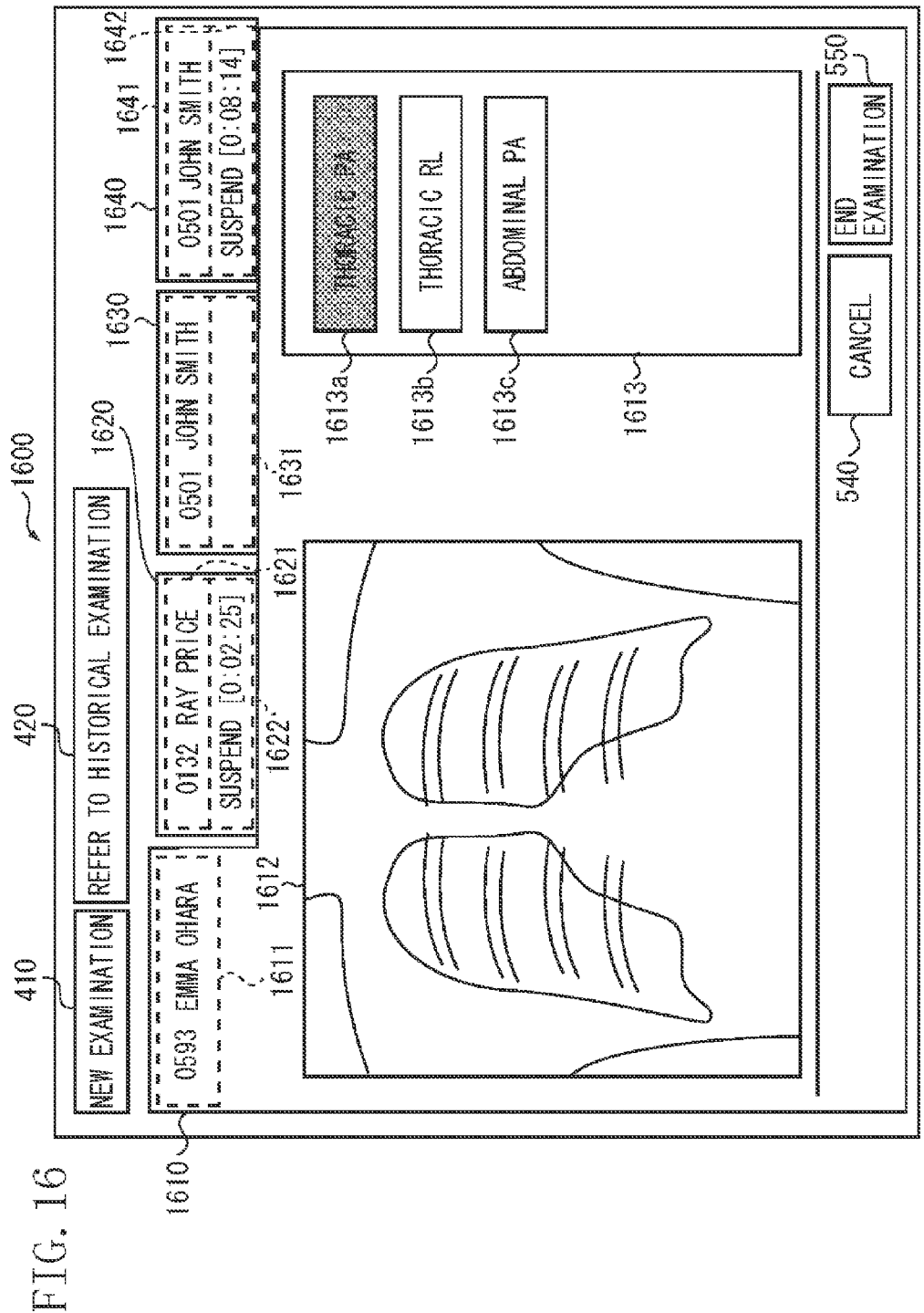
FIG. 16 illustrates a second embodiment of the present invention and is a schematic diagram illustrating an example of an examination screen displayed on the display unit in FIG. 2 when adding a historical examination reference operation of the same patient after commencing a new examination operation and adding two new examination operations.

FIG. 16 illustrates a second embodiment of the present invention and is a schematic diagram illustrating an example of an examination screen displayed on the display unit 117 in FIG. 2 when a historical examination reference operation of the same patient is added after commencing a new examination operation and two new examination operations are further added. The examination screen 1600 illustrated in FIG. 16 corresponds to the suspension information table in FIG. 15. In other words, the tab 1611 in the new examination content display unit 1620 illustrated in FIG. 16 corresponds to the tab 1 illustrated in FIG. 15 and the tab 1620, 1630 and 1640 illustrated in FIG. 16 correspond to the tabs 2-4 illustrated in FIG. 15.

A control operation is executed so that, of the suspended operations, the content of the suspended information table illustrated in FIG. 15 is used so that suspension information (in the example in FIG. 16, suspension information 1622 and 1642) is only displayed in the tab for the examination operation (in the example in FIG. 16, the tab 1620 and 1640). Consequently, the suspension information table illustrated in FIG. 15 in an inner section enables control so that suspension information is not displayed during suspension of operations which can remain suspended without causing problems.

In the X-ray imaging system 110 according to the second embodiment, control of the display, or non-display, of suspension information on a tab (header) for a suspension operation is performed according to the contents of the suspension operation. More specifically, when the contents of the suspension operation is an examination using X-ray imaging, the suspension information is displayed on the tab for the suspension operation and when the contents of the suspension operation is not an examination using X-ray imaging, the suspension information is not displayed on the tab for the suspended operations. In this manner, unnecessary information for an operation which can remain suspended without causing a problem is not displayed. Furthermore, it is possible to lay emphasis for an operator that the operation should not remain uncompleted.

A third embodiment of the present invention will be described hereafter. The schematic structure of the X-ray imaging system according to the third embodiment is the same as the schematic structure of the X-ray imaging system 100 according to the first embodiment illustrated in FIG. 1. The system for adding a new examination operation, the system for adding an historical examination reference operation and the process in the flowchart from commencement to completion of the examination operation in the third embodiment is the same as the first embodiment.

Figure 17:
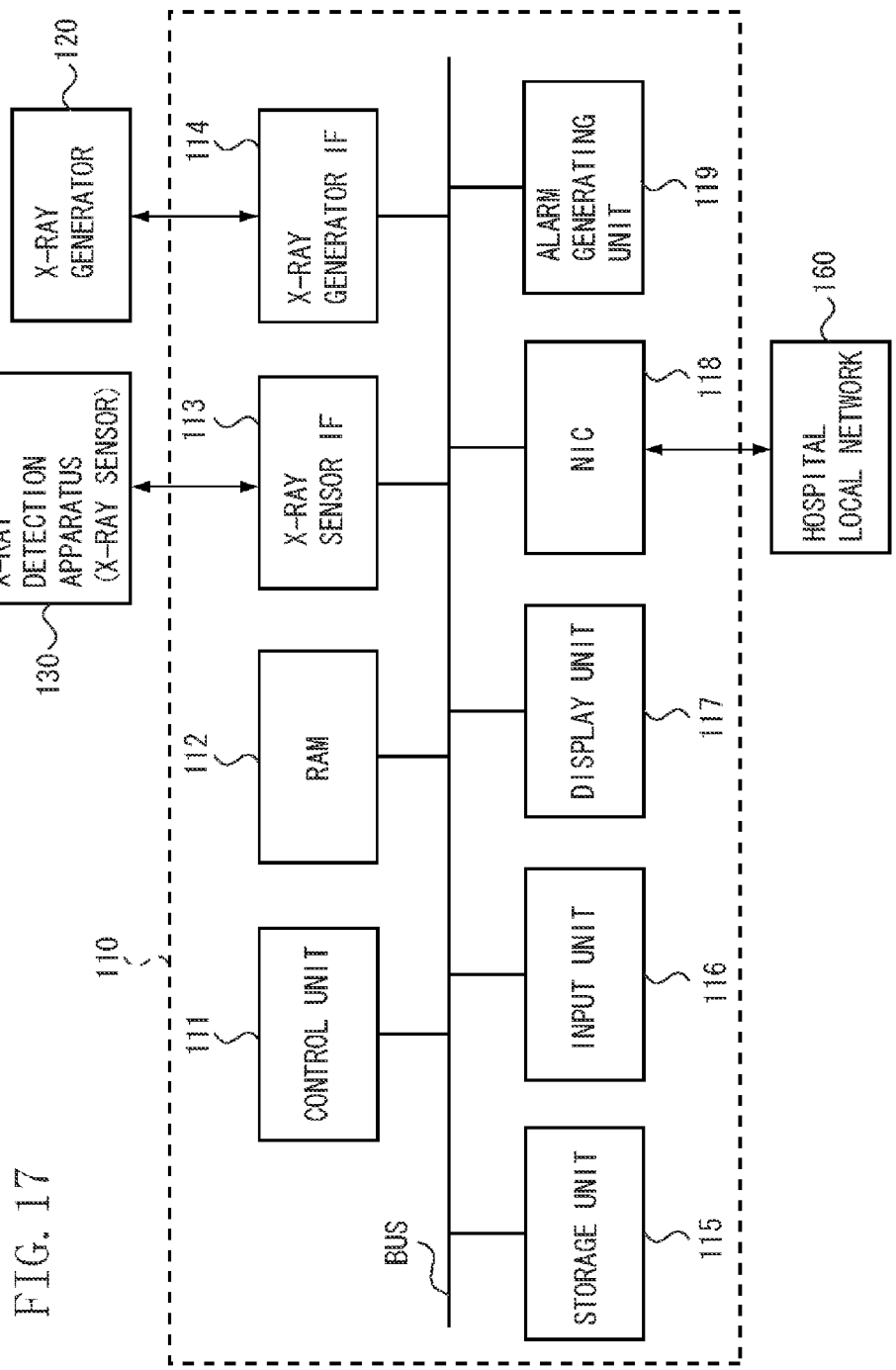
FIG. 17 is a schematic diagram illustrating an example of the inner arrangement of an X-ray imaging system (information processing system) according to a third embodiment of the present invention.

FIG. 17 is a schematic diagram illustrating an example of the inner arrangement of an X-ray imaging system (information processing system) according to a third embodiment of the present invention. In FIG. 17, those functions which are the same as FIG. 2 are denoted by the same reference numerals.

The X-ray imaging apparatus 110-2 according to the third embodiment illustrated in FIG. 17 includes the addition of an alarm generating unit 119 to the X-ray imaging apparatus 110 according to the first embodiment illustrated in FIG. 2. New limit time information is set as information held in the inner section (for example the storage unit 115) of the X-ray imaging apparatus 110-2. The limit time information is the information indicating the limit time (fixed period) for the suspension time for a suspended operation. When the suspension time reaches the limit time, the control unit 111, for example, controls the alarm generating unit 119 to produce an alarm. Furthermore, the control unit 111 stops generating an alarm sound by the alarm generating unit 119 when an operation exceeding the limit time is put into a current state.

According to the third embodiment, the effect of preventing a suspended operation from remaining incomplete can be improved.

A fourth embodiment of the present invention will be described hereafter. The schematic structure of the X-ray imaging system according to the fourth embodiment is the same as the schematic structure of the X-ray imaging system 100 according to the first embodiment illustrated in FIG. 1. The internal structure of the X-ray imaging apparatus according to the fourth embodiment is the same as the internal structure of the X-ray imaging system 110 according to the first embodiment illustrated in FIG. 2. Furthermore the system for adding a new examination operation, the system for adding an historical examination reference operation and the process in the flowchart from commencement to completion of the examination operation in the fourth embodiment is the same as the first embodiment.

In the first embodiment, a suspension time is displayed as the suspension information. However, the present invention is not limited to this display and instead of a suspension time, suspension sequence information may be displayed as suspension information.

Sequence information for suspension in the fourth embodiment is sequence information for the removal of the focus of the current operation, information for the initial removal of the focus of the current operation or sequence information when the accumulated time for all suspension periods is long. In the present embodiment, instead of a suspension time, sequence information for the suspension is displayed as suspension information in the form of 1, 2, 3 . . . in order from the longest suspension time in the first embodiment. The same effect as the first embodiment can be obtained by the display of sequence information for suspension in such a manner.

The steps in FIG. 3, FIG. 6 and FIG. 9 illustrating the control method of the X-ray imaging apparatus 110 and the processing of each unit illustrated in FIG. 2 forming the X-ray imaging apparatus 110 according to each embodiment above are realized by executing a program stored by the CPU of the computer in a storage medium. The program and a computer-readable storage medium storing the program are included in the present invention.

The present invention may be embodied as a system, apparatus, method, program or storage medium. More specifically, the present invention may be applied to a system configured from a plurality of devices and may also be applied to an apparatus configured from a single device.

The present invention includes a configuration in which a software program executing the functions of each embodiment above (programs corresponding to the embodiments in the flowcharts in FIG. 3, FIG. 6 and FIG. 9) may be supplied directly or remotely to a system or apparatus. The invention may also be realized by reading a program code supplied by a computer in the system or apparatus.

Thus, the program code itself installed in the computer realizes the present invention by realizing the processing functions of the present invention with a computer.

In that case, as long as program functions are provided, those functions may be in the form of script data supplied to operating system or a program executed by an interpreter or, an object code.

The storage medium configured to supply the program may, for example, be a flexible disk, hard disk, optical disk, magneto-optical disk, magneto-optic, CD-ROM, CD-R and CD-RW. A magnetic tape, non-volatile memory card, ROM, DVD (DVD-ROM, DVD-R) may also be used.

In addition, the method of supplying programs includes connection to a homepage on the Internet using a browser of a client computer. The computer program itself for the present invention or a compressed file having an automatic installation function may be supplied by downloading onto a storage medium such as a hard disk.

The program code configuring the program for the present invention may be divided into a plurality of files and may be realized by downloading those respective files from different homepages. In other words, a WWW server enabling download of program files realizing the functions processes of the present invention on a computer, to a plurality of users is also included within the scope of the invention.

The program of the present invention may be encrypted, stored in a storage medium such as a CD-ROM and distributed to a user. Information for keys for the unlocking of the encryption may be downloaded from a homepage via the Internet by user satisfying predetermined conditions. Then the downloaded key information may be used to unlock and execute the programs and install the programs on a computer.

The functions of each embodiment above may be realized by executing the program read by a computer. In addition, an operating system performed in a computer may perform all or a part of actual processing operation using instructions from the program and thereby realize the functions of each embodiment above by such process operations.

The programs read from a storage medium may be written into a memory provided in a function expansion unit connected to a computer or a function expansion board inserted into the computer. Then, the instructions from the program may be used to perform a part of the whole of the actual processing operation by the CPU or the like provided in the function expansion board or function expansion unit and thereby realize the above functions of each embodiment by such process operations.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-048510 filed Mar. 2, 2009, which is hereby incorporated by reference herein in its entirety.

What is claimed is:

1. An information processing apparatus configured to execute a plurality of operations in parallel comprising:
a display unit configured to display a header which identifies each operation in a plurality of operations;
a switching unit configured to switch a current operation based on selection of the header; and
a display control unit which, when a current operation is switched using the switching unit, controls display of suspension information to indicate a suspension state of a suspended operation on the header for a suspended operation in addition to the current operation,
wherein the display control unit performs control to make display or non-display of suspension information on the header for a suspended operation according to the content of the suspended operation,
wherein the information processing apparatus is an X-ray imaging apparatus and the display control unit displays suspension information on a header for a suspended operation when the suspended operation is an examination using X-ray imaging, and the suspension information is not displayed on the header for the suspended operation when the suspended operation is not an examination using an X-ray imaging.

2. The information processing apparatus according to claim 1, wherein the display control unit displays suspension information on the header for the suspended operation at a timing of the removal of the focus for the current operation.

3. The information processing apparatus according to claim 1, further comprising:
a time measurement unit configured to measure time; and
the display control unit displays a suspension time from the time of removal of the focus in the current operation, which is measured by the time measurement unit, as suspension information.

4. The information processing apparatus according to claim 3, wherein the suspension time is the time from the time of first removal of the focus in the current operation.

5. The information processing apparatus according to claim 3, further comprising an alarm generating unit for generating an alarm, which generates an alarm when the suspension time reaches a predetermined time.

6. The information processing apparatus according to claim 1, wherein the suspension information is the suspension time calculated by summing all suspension periods.

7. The information processing apparatus according to claim 1, wherein the suspension information is sequence information for removal of the focus in the current operation, sequence information for first removal of focus in the current operation, or sequence information for a long suspension time calculated by summing all suspension periods.

8. The information processing apparatus according to claim 1, wherein the information processing apparatus is an X-ray imaging apparatus and the header is a GUI tab.

9. A method of controlling an information processing apparatus configured to execute a plurality of operations in parallel, the method comprising:
displaying a header configured to identify each operation in a plurality of operations, on a display unit;
switching a current operation based on the selection of the header; and
controlling display of suspension information to indicate a suspension state of a suspended operation on the header for a suspended operation in addition to the current operation when switching the current operation and to make display or non-display of suspension information on the header for a suspended operation according to the content of the suspended operation.

10. A non-transitory computer program for causing a computer to execute a method for controlling an information processing apparatus configured to execute a plurality of operations in parallel, the method comprising:
displaying a header configured to identify each operation in a plurality of operations on a display unit;
switching a current operation based on selection of the header; and
controlling display of suspension information to indicate a suspension state of a suspended operation on the header for a suspended operation in addition to the current operation when switching the current operation and to make display or non-display of suspension information on the header for a suspended operation according to the content of the suspended operation.

11. An information processing apparatus configured to execute a plurality of operations in parallel comprising:
a display unit configured to display a header which identifies each operation in a plurality of operations;
a switching unit configured to switch a current operation based on selection of the header; and
a display control unit which, when a current operation is switched using the switching unit, controls display of suspension information to indicate a suspension state of a suspended operation on the header for a suspended operation in addition to the current operation,
wherein the display control unit performs control to make display or non-display of suspension information on the header for a suspended operation according to the content of the suspended operation.

12. The information processing apparatus according to claim 11, wherein the display control unit displays suspension information on the header for the suspended operation at a timing of the removal of the focus for the current operation.

13. The information processing apparatus according to claim 11, further comprising:
a time measurement unit configured to measure time; and
the display control unit displays a suspension time from the time of removal of the focus in the current operation, which is measured by the time measurement unit, as suspension information.

14. The information processing apparatus according to claim 13, wherein the suspension time is the time from the time of first removal of the focus in the current operation.

15. The information processing apparatus according to claim 11, wherein the suspension information is the suspension time calculated by summing all suspension periods.

16. The information processing apparatus according to claim 13, further comprising an alarm generating unit for generating an alarm, which generates an alarm when the suspension time reaches a predetermined time.

17. The information processing apparatus according to claim 11, wherein the suspension information is sequence information for removal of the focus in the current operation, sequence information for first removal of focus in the current operation, or sequence information for a long suspension time calculated by summing all suspension periods.

18. The information processing apparatus according to claim 11, wherein the information processing apparatus is an X-ray imaging apparatus and the header is a GUI tab.

* * * * *